US011623055B2

(12) United States Patent
Cole, Jr. et al.

(10) Patent No.: US 11,623,055 B2
(45) Date of Patent: Apr. 11, 2023

(54) PRESSURE GENERATOR INLET FILTER APPARATUS

(71) Applicant: KONINKLIJKE PHILIPS N.V., Eindhoven (NL)

(72) Inventors: Kenneth E. Cole, Jr., New Alexandria, PA (US); Richard Paul Alfieri, Delmont, PA (US); Mark Wayne Barclay, Saxonburg, PA (US)

(73) Assignee: Koninklijke Philips N.V., Eindhoven (NL)

( * ) Notice: Subject to any disclaimer, the term of this patent is extended or adjusted under 35 U.S.C. 154(b) by 383 days.

(21) Appl. No.: 16/465,369

(22) PCT Filed: Dec. 7, 2017

(86) PCT No.: PCT/EP2017/081797
§ 371 (c)(1),
(2) Date: May 30, 2019

(87) PCT Pub. No.: WO2018/104437
PCT Pub. Date: Jun. 14, 2018

(65) Prior Publication Data
US 2019/0388633 A1     Dec. 26, 2019

Related U.S. Application Data

(60) Provisional application No. 62/430,970, filed on Dec. 7, 2016.

(51) Int. Cl.
*A61M 16/10*     (2006.01)
*A61M 16/00*     (2006.01)
(Continued)

(52) U.S. Cl.
CPC ...... *A61M 16/0057* (2013.01); *A61M 16/107* (2014.02); *A61M 2202/0208* (2013.01);
(Continued)

(58) Field of Classification Search
CPC ..... A47J 31/605; A61L 9/03; A61M 16/0057; A61M 16/105; A61M 16/1055;
(Continued)

(56) References Cited

U.S. PATENT DOCUMENTS 2,201,650 A *   5/1940   Hallerberg ........... F02M 35/026
                                                       96/348
2,959,247 A      11/1960   Sare
(Continued)

FOREIGN PATENT DOCUMENTS

CN        205478403 U     8/2016
DE    102015002052 A1     8/2016
(Continued)

OTHER PUBLICATIONS

PCT International Search Report, International application No. PCT/EP2017/081797, dated Mar. 7, 2018.
(Continued)

*Primary Examiner* — Annette Dixon
(74) *Attorney, Agent, or Firm* — Daniel H. Brean; Andrew M. Gabriel (57) ABSTRACT

The present disclosure pertains to a therapeutic gas delivery system (8) including a pressure generator inlet apparatus (10) configured to facilitate filtering of gas drawn into the inlet (14) of the pressure generator (16) of the system. The apparatus comprises a body (12) and a support (24). The body is configured to removably engage the inlet of the pressure generator and receive a particulate filter (18). The body forms an orifice (19) configured to conduct gas that has passed through the filter to the pressure generator inlet. The support is coupled to the body at or near the orifice. The support is configured to extend from the body toward the filter and support the filter. The support is configured to resist (Continued)

collapse of the filter into the orifice caused by gas flowing through the filter to the pressure generator inlet.

20 Claims, 9 Drawing Sheets

(51) Int. Cl.
  *A62B 23/02* (2006.01)
  *F04D 29/70* (2006.01)
(52) U.S. Cl.
  CPC .......... *A62B 23/02* (2013.01); *B01D 2265/06* (2013.01); *F04D 29/70* (2013.01)
(58) Field of Classification Search
  CPC ........ A61M 16/107; A61M 2202/0208; A62B 23/02; B01D 2253/102; B01D 2259/4541; B01D 2265/06; B01D 2275/10; B01D 25/12; B01D 25/26; B01D 29/012; B01D 37/02; B01D 46/0001; B01D 46/10; B01D 46/103; B01D 46/106; B01D 46/30; B01D 46/521; B01D 46/523; B01D 53/0415; B29C 65/0672; B29C 65/08; B29C 66/1312; B29C 66/5412; B29L 2031/14; C02F 1/688; F02F 7/006; F02M 35/02; F02M 35/024; F04D 29/70; F04D 29/703; Y10S 55/33; Y10S 55/35; Y10T 29/49808; Y10T 29/49918
  See application file for complete search history.

(56) References Cited

U.S. PATENT DOCUMENTS

| | | | | |
|---|---|---|---|---|
| 3,339,533 | A * | 9/1967 | Ingemar | F02M 35/02 123/572 |
| 3,681,898 | A * | 8/1972 | Hopkins | F02M 35/024 55/487 |
| 3,686,837 | A * | 8/1972 | Hopkins | B01D 46/521 55/487 |
| 3,782,083 | A * | 1/1974 | Rosenberg | B01D 46/10 55/491 |
| 3,884,658 | A * | 5/1975 | Roach | F02M 35/08 55/482 |
| 4,199,334 | A * | 4/1980 | Berkhoel | B01D 46/2411 55/497 |
| 4,379,051 | A * | 4/1983 | Hiesinger | B01D 25/26 210/193 |
| 4,543,112 | A * | 9/1985 | Ackley | A62B 23/02 128/205.27 |
| 4,548,626 | A * | 10/1985 | Ackley | B01D 46/106 128/201.25 |
| 7,419,526 | B2 * | 9/2008 | Greer | A62B 23/02 55/512 |
| 9,933,116 | B2 * | 4/2018 | Lee | F02M 21/0227 |
| 2008/0185331 | A1 | 8/2008 | Sato | |
| 2009/0223368 | A1 | 9/2009 | Augustine | |
| 2010/0071323 | A1 | 3/2010 | Cosgrove | |
| 2012/0138058 | A1 | 6/2012 | Fu | |
| 2013/0298512 | A1 | 11/2013 | Symons | |
| 2013/0306072 | A1 | 11/2013 | Moir | |

FOREIGN PATENT DOCUMENTS

| | | | | |
|---|---|---|---|---|
| EP | | 420812 A * | 4/1991 | .......... A62B 18/006 |
| EP | | 0688949 A1 | 12/1995 | |
| WO | WO-8606643 A1 * | | 11/1986 | .......... A62B 18/006 |
| WO | WO2004108198 A1 | | 12/2004 | |
| WO | WO2015174084 A1 | | 11/2015 | |

OTHER PUBLICATIONS

CartridgeFilterGuide_pgs_HR.pdf Downloaded from Internet Jul. 29, 2016 (Date Kenneth Cole sent it).

* cited by examiner

METHOD 1200

Removably engage an inlet of a pressure generator and receive a particulate filter with a body of a pressure generator inlet assembly
1202

Couple a support to the body to resist collapse of the filter into an orifice of the body caused by gas flowing through the filter to the pressure generator inlet
1204

FIG. 12

PRESSURE GENERATOR INLET FILTER APPARATUS

CROSS-REFERENCE TO RELATED APPLICATIONS

This patent application claims the priority benefit under 35 U.S.C. § 371 of international patent application no. PCT/EP2017/081797, filed Dec. 7, 2017, which claims the priority benefit under 35 U.S.C. § 119(e) of U.S. Provisional Application No. 62/430,970, filed on Dec. 7, 2016, the contents of which are herein incorporated by reference.

BACKGROUND OF THE INVENTION

1. Field of the Invention

The present disclosure pertains to a therapeutic gas delivery system including a pressure generator inlet apparatus configured to facilitate filtering of gas drawn into the inlet of the pressure generator of the system.

2. Description of the Related Art

Two-sided disc, or pancake, filters are known. These filters are used in half and full-face personal respirators (e.g., gas masks) where gas is drawn into the respirators at low pressures and/or flow rates. These filters are not used in therapeutic gas delivery systems because gas is drawn into such systems at (higher) pressures and/or flow rates that cause collapse of the pancake filters.

SUMMARY OF THE INVENTION

Accordingly, one or more aspects of the present disclosure relate to a pressure generator inlet apparatus. The apparatus comprises a body, a support, and/or other components. The body is configured to removably engage an inlet of a pressure generator and receive a particulate filter. The body forms an orifice configured to conduct gas that has passed through the filter to the pressure generator inlet. The support is coupled to the body at or near the orifice. The support is configured to extend from the body toward the filter and support the filter. The support is configured to resist collapse of the filter into the orifice caused by gas flowing through the filter to the pressure generator inlet. In some embodiments, the filter is a two-sided disc filter. In some embodiments, the two-sided disc filter is a pancake filter. In some embodiments, the body is configured to couple with the inlet on a first side of the body and receive the filter on a second side of the body opposite the first side. In some embodiments, the support is a protrusion, and the protrusion is configured to extend from the second side of the body toward the filter and support the filter.

Another aspect of the present disclosure relates to a method for filtering gas drawn into a pressure generator with a pressure generator inlet apparatus. The apparatus comprises a body, a support, and/or other components. The method comprises: removably engaging, with the body, an inlet of the pressure generator and receiving, with the body, a particulate filter. The body forms an orifice configured to conduct gas that has passed through the filter to the pressure generator inlet. The method further comprising coupling the support to the body at or near the orifice. The support is configured to extend from the body toward the filter and support the filter. The support is configured to resist collapse of the filter into the orifice caused by gas flowing through the filter to the pressure generator inlet. In some embodiments, the filter is a two-sided disc filter. In some embodiments, the two-sided disc filter is a pancake filter. In some embodiments, the body couples with the inlet on a first side of the body and receives the filter on a second side of the body opposite the first side. In some embodiments, the support is a protrusion, and the protrusion extends from the second side of the body toward the filter and supports the filter.

Still another aspect of present disclosure relates to a pressure generator inlet apparatus comprising: means for removably engaging an inlet of a pressure generator and receiving a particulate filter, the means for engaging and receiving forming an orifice configured to conduct gas that has passed through the filter to the pressure generator inlet; and means for supporting the filter, the means for supporting coupled to the body at or near the orifice, the means for supporting configured to extend from the means for engaging and receiving toward the filter to support the filter, the means for supporting configured to resist collapse of the filter into the orifice caused by gas flowing through the filter to the pressure generator inlet. In some embodiments, the filter is a two-sided disc filter. In some embodiments, the two-sided disc filter is a pancake filter. In some embodiments, the means for engaging and receiving couples with the inlet on a first side of the means for engaging and receiving, and receives the filter on a second side of the means for engaging and receiving opposite the first side. In some embodiments, the means for supporting includes a protrusion. In some embodiments, the protrusion extends from the second side of the means for engaging and receiving toward the filter and supports the filter.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
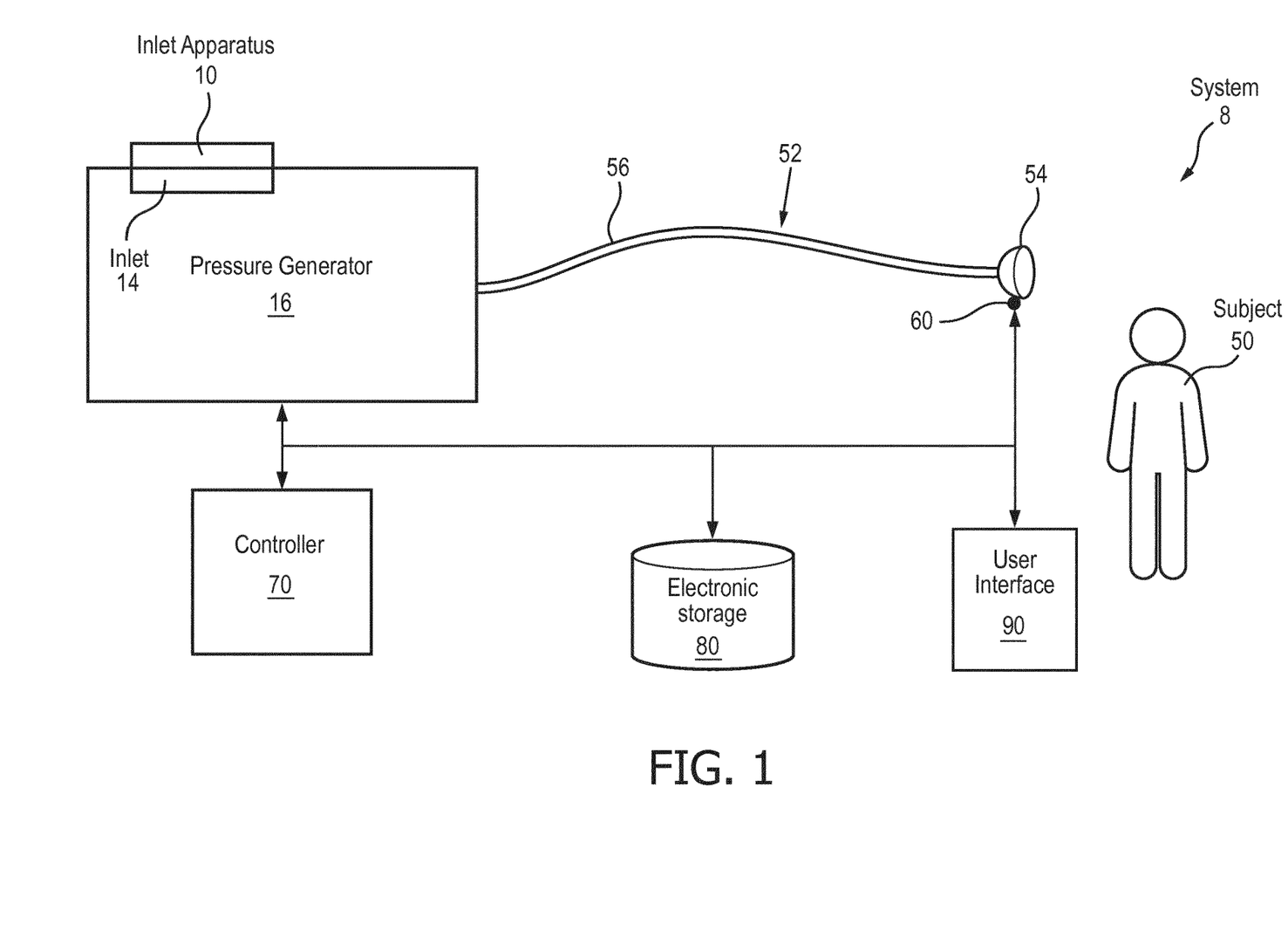
FIG. 1 is a schematic illustration of a therapeutic gas delivery system including a pressure generator inlet apparatus configured to facilitate filtering of gas drawn into an inlet of a pressure generator in the system.

FIG. 1 is a schematic illustration of a therapeutic gas delivery system 8 including a pressure generator inlet apparatus 10 configured to facilitate filtering of gas drawn into an inlet 14 of a pressure generator 16 in system 8. In some embodiments, system 8 comprises one or more of inlet apparatus 10, pressure generator 16, a gas delivery flow path 52, one or more sensors 60, a controller 70, electronic storage 80, a user interface 90, and/or other components.

Figure 2:
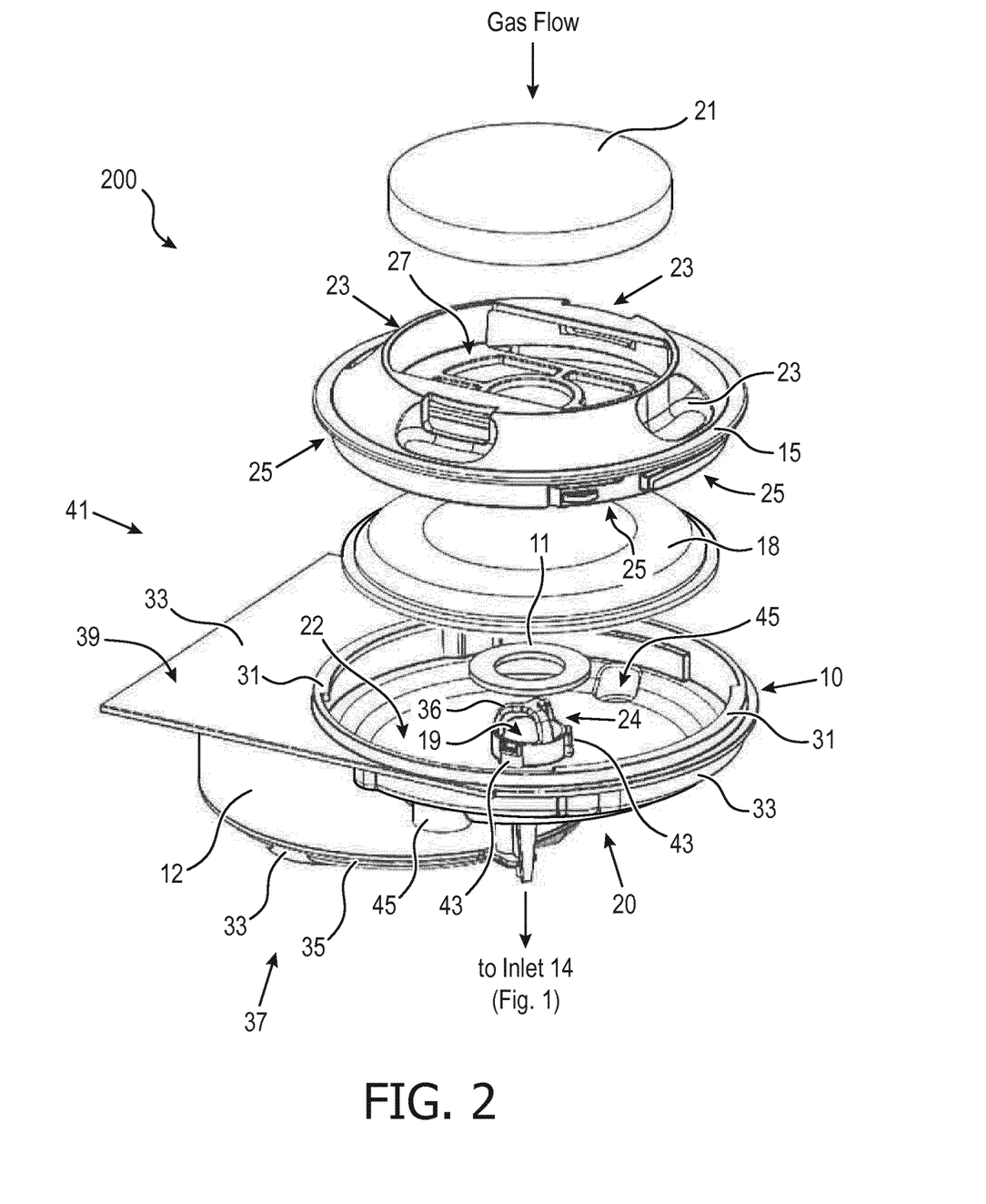
FIG. 2 illustrates a muffler assembly for the pressure generator inlet that includes the inlet apparatus.

FIG. 2 illustrates a muffler assembly 200 for inlet 14 (FIG. 1) of pressure generator 16 (FIG. 1). In some embodiments, as shown in FIG. 2, apparatus 10 is included in muffler assembly 200. Apparatus 10 facilitates the use of commercially available two-sided disc pancake filters 18 and/or other filters to filter gas drawn into system 8 (FIG. 1) via inlet 14 of pressure generator 16. Typically, these filters are used in half and full-face personal respirators (e.g., gas masks) where gas is drawn into the respirators at low pressures and/or flow rates. For a normal, healthy adult, mean generated pressure is around 5 cmH$_2$O. Typical flow rates are about 30-60 liters per minute (lpm). For example, these commercially available pancake filters include the 3M 2000 Series of filters and/or other filters. These filters provide minimal resistance, are highly efficient (e.g., 99.97%), are regulated by the National Institute for Occupational Safety and Health (NIOSH), have a widely accepted user interface, are readily available, are inexpensive, and would filter particulate that would otherwise pass into a typical therapeutic gas delivery system if used with a therapeutic gas delivery system. However, until now, these filters have not been used in therapeutic gas delivery systems because gas is drawn into such systems at (higher) pressures and/or flow rates (e.g., up to about 40 cmH$_2$O at up to about 225 lpm) that cause collapse of the pancake filters. Collapse of a pancake filter into inlet 14 of pressure generator 16 would increase the pressure drop across inlet 14 and limit the ability of pressure generator 16 to generate pressures for therapeutic applications (e.g., as described below).

In some embodiments, muffler assembly 200 includes apparatus 10, a gasket 11, two-sided disc pancake particulate filter 18, a cover 15, a gross particulate filter 21, and/or other components. Gas flows into inlet 14 (FIG. 1) of pressure generator 16 (FIG. 1) after passing through gross particulate filter 21, cover 15, filter 18, and apparatus 10. Gross particulate filter 21 is configured to perform an initial filtration on gas entering muffler assembly 200. Initial filtration comprises filtering particles from gas passing through filter 21 that are about 0.017 inch or larger. In some embodiments, gross particulate filter 21 may be similar to and/or the same as an inlet filter on a home dehumidifier and/or other filters. Gross particulate filter 21 is shown in FIG. 2 having a round shape. This is not intended to be limiting. Gross particulate filter may have any shape and/or size that facilitates coupling with cover 15 and/or other components of muffler assembly 200. Cover 15 comprises coupling features 23 configured to couple with filter 21.

Cover 15 also comprises coupling features 25 configured to couple with apparatus 10 to hold filter 18 between cover 15 and apparatus 10. Cover 15 further comprises orifices 27 that facilitate conducting gas that has passed through filter 21 to filter 18. Coupling features 23 and 25 may include grooves, slots, depressions, orifices, clamps, surface shapes, ramped locking features, compression locking features, and/or other features (this list and the illustration in FIG. 2 is not intended to be limiting) that facilitate coupling the components of muffler assembly 200. Gasket 11 is configured to facilitate receipt of filter 18 by apparatus 10. Gasket 11 may have any shape and/or size, and/or be made from any material that allows apparatus 10 to function as described herein. In some embodiments, gasket 11 may be similar to and/or the same as a gasket made by 3M (e.g., 3M part number 6895) and/or other gaskets.

Apparatus 10 comprises a body 12, a support 24, and/or other components. Body 12 removably couples with inlet 14 (FIG. 1) of pressure generator 16 (FIG. 1). Body 12 receives filter 18. As described above, in some embodiments, filter 18 is a two-sided disc filter and/or other filters. In some embodiments, the two-sided disc filter is a pancake filter and/or other filters. Body 12 forms an orifice 19 configured to conduct gas that has passed through filter 18 to pressure generator inlet 14. In some embodiments, body 12 couples with inlet 14 on a first side 20 of body 12 and receives filter 18 on a second side 22 of body 12 opposite the first side. In some embodiments, one or more portions of second side 22 may have a shape that corresponds to the shape of filter 18 and/or other shapes. In some embodiments, body 12 includes filter locking features 43 (e.g., clips, clamps, grooves, channels, and/or other features) configured to facilitate removably coupling filter 18 to body 12. The filter locking features may be located at or near orifice 19 (as shown in FIG. 2) and/or in other locations.

In some embodiments, body 12 includes coupling components 31 (e.g., ramped locking features, compression locking features, and/or other features) that facilitate coupling with cover 15 and/or other components of muffler assembly 200, coupling components 33 (e.g., grooves, surfaces, channels, angled surfaces, and/or other features) configured to facilitate coupling and/or seating of body 12 and/or muffler assembly 200 with and/or in pressure generator 16, and/or other coupling components. In some embodiments, a shape and/or size of coupling features in 33 corresponds to a shape and/or size of coupling features in pressure generator 16 to facilitate coupling between body 12 and/or muffler assembly 200 and pressure generator 16. For example, as shown in FIG. 2, coupling components 33 include a seating plate 35 located at a first end 37 of muffler assembly 200 and a seating surface 39 on a side 41 of muffler assembly 200 that facilitate coupling with pressure generator 16. Coupling components 33 include orifices 45 configured to receive screws and/or other coupling components that engage corresponding features (e.g., threads) in pressure generator 16, and/or other components.

Figure 3:
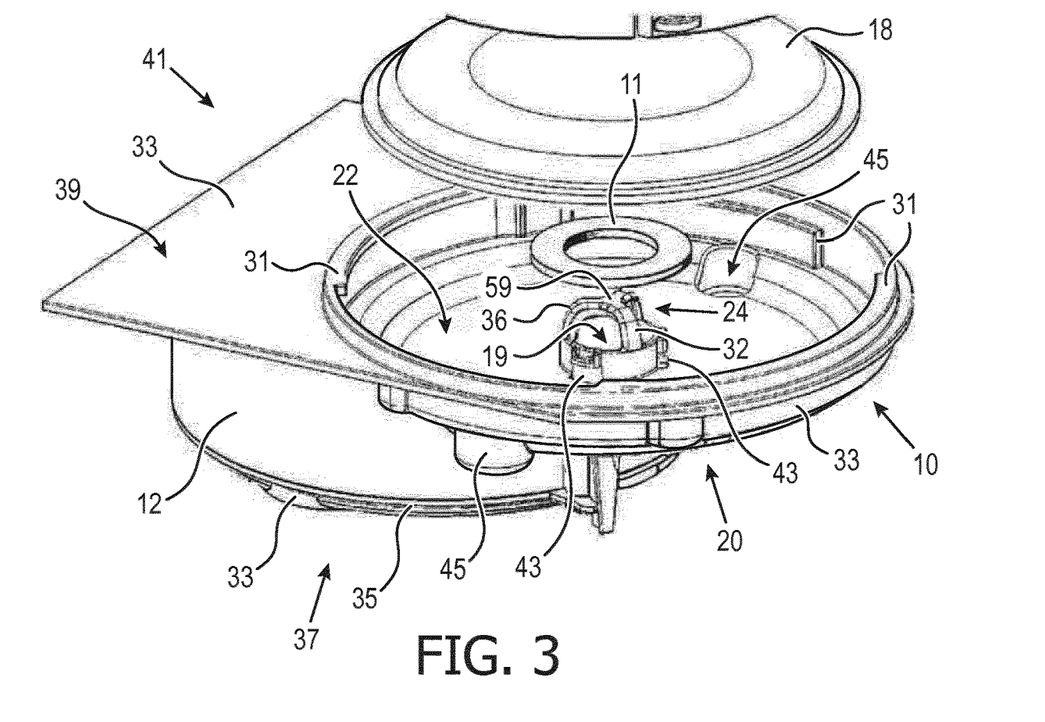
FIG. 3 illustrates an enlarged view of a body of the apparatus receiving a gasket and a filter.
Figure 4:
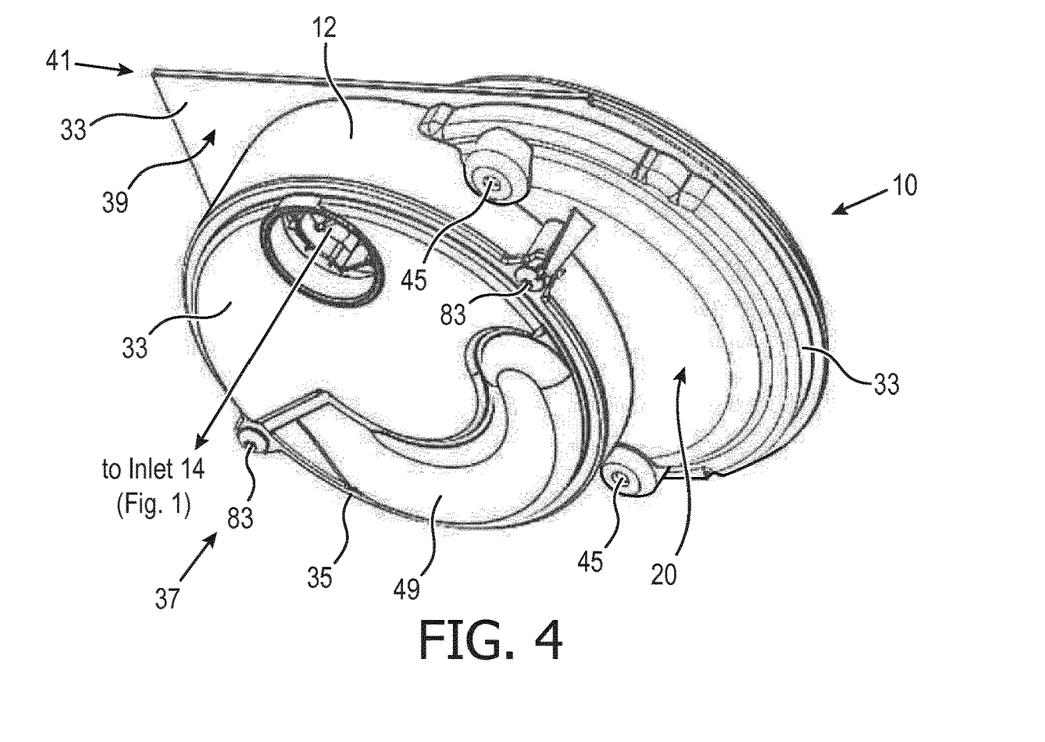
FIG. 4 illustrates a view of the body from an end of the muffler assembly.
Figure 5:
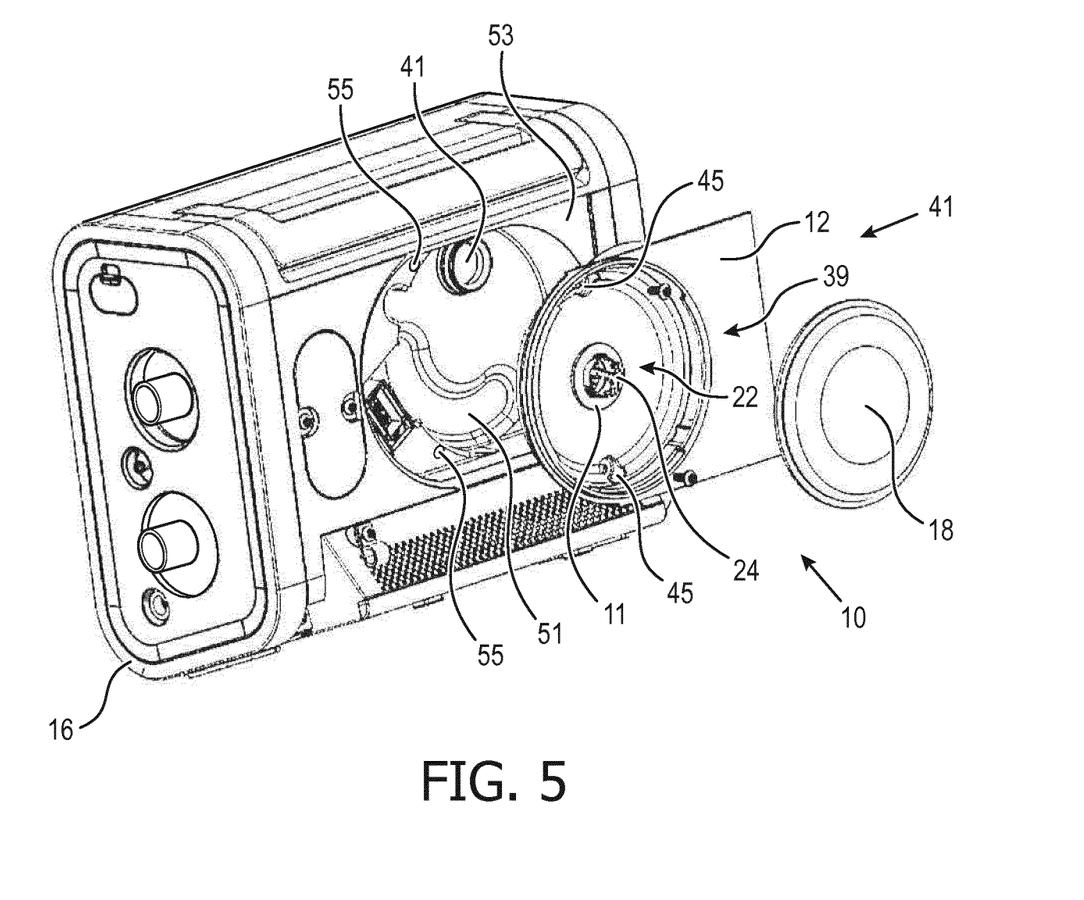
FIG. 5 illustrates coupling the body and the filter with the pressure generator.

By way of a non-limiting example, FIG. 3 illustrates an enlarged view of body 12 receiving gasket 11 and filter 18. FIG. 4 illustrates a view of body 12 from end 37 of muffler assembly 200 (FIG. 2). FIG. 5 illustrates coupling body 12 and filter 18 with pressure generator 16. As shown in FIG. 4, seating plate 35 is coupled to body 12 via screws 83 and/or other coupling mechanisms. As shown in FIG. 4 and FIG. 5, seating plate 35 includes seating features 49 (FIG. 4) that correspond to receiving features 51 (FIG. 5) in pressure generator 16. Seating surface 39 (FIG. 4) corresponds to a portion 53 (FIG. 5) of pressure generator 16 configured to receive seating surface 39. Orifices 45 (FIG. 4 and FIG. 5) receive screws and/or other coupling components that engage corresponding features 55 (e.g., threads) in pressure generator 16.

Figure 6:
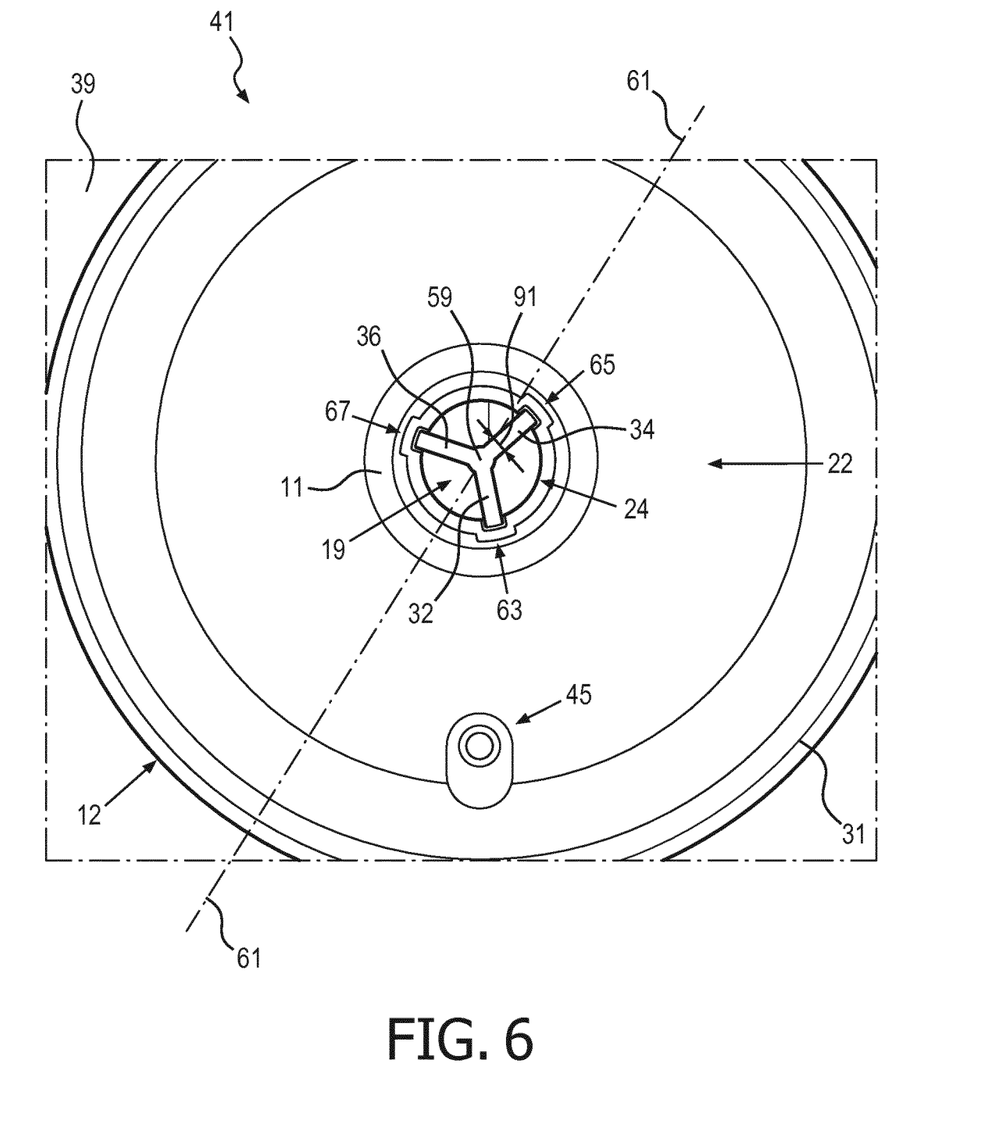
FIG. 6 illustrates a support of the inlet apparatus coupled to the body.

FIG. 6 illustrates support 24 coupled to body 12. Support 24 is configured to extend from body 12 toward filter 18 and support filter 18 (e.g., as shown in FIG. 2). Support 24 resists collapse of filter 18 into orifice 19 of body 12 and/or into inlet 14 (FIG. 1) of pressure generator 16 (FIG. 1). Collapse of filter 18 into orifice 19 (and/or inlet 14) may be caused by gas flowing through filter 18 to pressure generator inlet 14 and/or other forces. Support 24 may prevent collapse of filter 18 while still substantially maximizing a free flow cross-sectional area through orifice 19 to reduce pressure drop across orifice 19 and inlet 14. Support 24 is coupled to body 12 at or near orifice 19. In some embodiments, support 24 is a protrusion, and extends from second side 22 of body 12 toward filter 18 to support filter 18.

In some embodiments, support 24 comprises three arcuate members 32, 34, 36, and/or other components. In some embodiments, support 24 comprises more or less than three arcuate members. In some embodiments, support 24 comprises one or more non-arcuate members. In some embodiments, an individual arcuate member 32, 34, and/or 36 has one end coupled to an edge of orifice 19 at or near second side 22 of body 12 and an opposite end coupled to the other arcuate members in a protruding position 59 relative to second side 22 of body 12. In some embodiments, orifice 19 has a circular cross-section with a central axis 61, and the opposite ends of the arcuate members 32, 34, and/or 36 are coupled in protruding position 59 at a location that corresponds to central axis 61 of circular orifice 19. For example, in FIG. 6, protruding position 59 lies along central axis 61.

In some embodiments, ends of arcuate members 32, 34, and/or 36 are positioned at substantially equidistant positions 63, 65, 67, and/or other locations around a circumference of orifice 19. In some embodiments, orifice 19 has a diameter of up to about 1 inch. In some embodiments, orifice 19 has a diameter between about 0.5 inches and about 1 inch. In some embodiments, orifice 19 has a diameter of about 0.75 inches. In some embodiments, arcuate members 32, 34, and/or 36 have a width 91, a thickness 93 (FIG. 7), and/or positions 63, 65, 67 configured such that support 24 is capable of supporting force exerted on support 24 by filter 18 and/or other forces. Width 91, thickness 93, and/or positions 63, 65, 67 may depend on the material used to fabricate support 24, a diameter of orifice 19, the magnitude and/or direction of force exerted on support 24, and/or other factors.

In some embodiments, support 24 may be manufactured in various ways, including but not limited to plastic injection molding, metal working and/or fabrication, and/or using other methods. In some embodiments, support 24 is coupled to body 12 via coupling components such as adhesive; screws, nuts, bolts, clips, clamps, hooks, and/or other coupling devices; slots, grooves, channels and/or other surface features in body 12; and/or other coupling components. In some embodiments, support 24 may be integral to body 12. By way of a non-limiting example, the example of support 24 shown in FIG. 6 was injection molded and "by-pass" steel was used to create the features (e.g., as described herein) of support 24.

Figure 7:
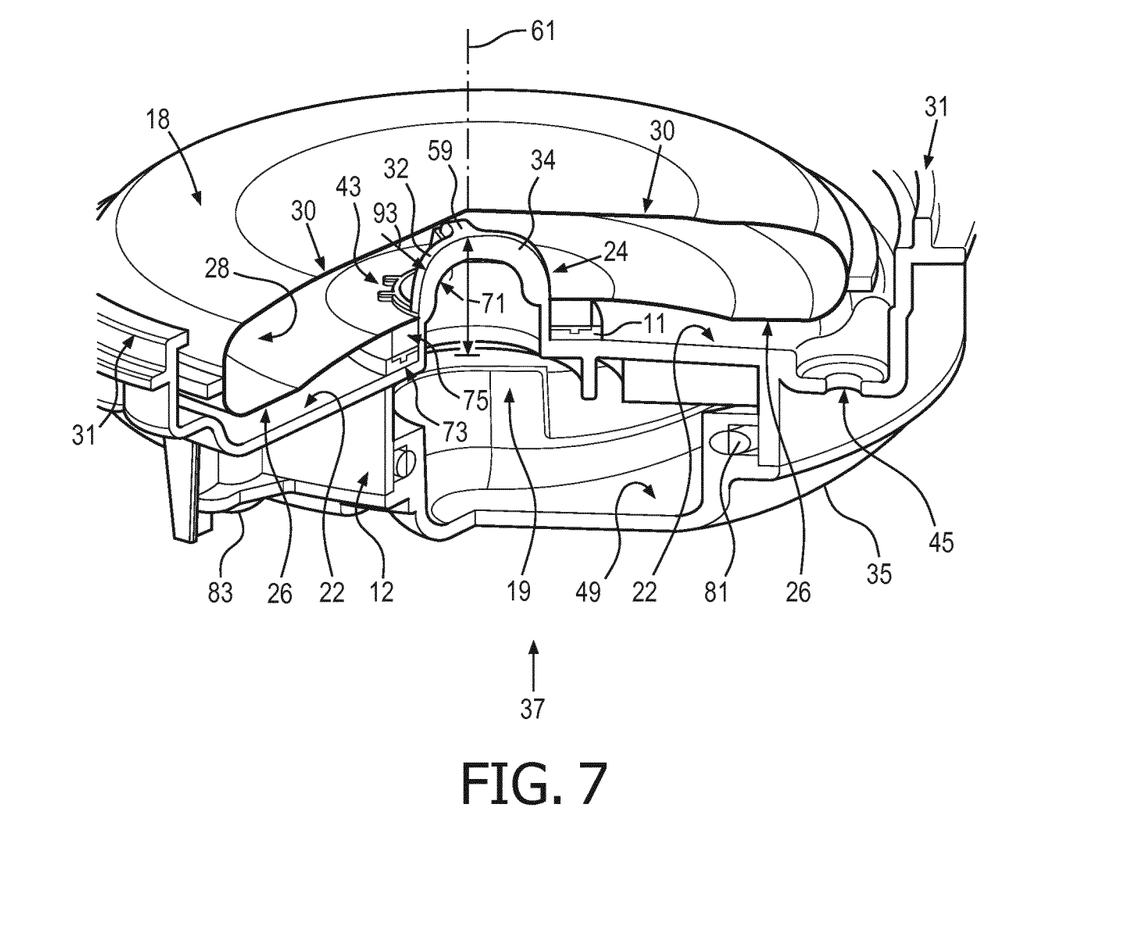
FIG. 7 illustrates extension of the support from a second side of the body.

FIG. 7 illustrates a cutaway view of body 12 and filter 18. As shown in FIG. 7, seating plate 35 is coupled to body 12 via a sealing ring 81 and/or other coupling mechanisms. Seating features 49 may form a flow path configured to conduct gas from orifice 19 to pressure generator inlet 14 (not shown in FIG. 7). Responsive to being received by body 12 (e.g., via a corresponding groove 73 in gasket 11 and alignment feature 75 on filter 18, and/or other components as illustrated in FIG. 1), a first side 26 of pancake filter 18 engages second side 22 of body 12. In some embodiments, support 24 extends from second side 22 a distance 71 of up to about 1 inch. In some embodiments, support 24 extends from second side 22 a distance 71 of between about 0.5 inches and about 1 inch. In some embodiments, support 24 extends from second side 22 a distance 71 of between about 0.68 inches and about 0.75 inches. Support 24 extends past first side 26 of pancake filter 18 into an inside 28 of pancake filter 18 to support a second, opposite, side 30 of pancake filter 18 from inside 28. For example, as shown in FIG. 7, support 24 is configured such that the inside of side 30 engages protruding position 59 of support 24.

The description of coupling support 24 to body 12 at the edge of orifice 19, the description of support 24 formed by arcuate members 32, 34, and 36, and the dimensions described herein are not intended to be limiting. Support 24 may be coupled to body 12 by any coupling components and have any shape that allows apparatus 10 to function as described herein. Support 24 may be coupled with body 12 by any coupling method and/or have any shape that prevents collapse of filter 18 into orifice 19 and/or inlet 14 (FIG. 1) of pressure generator 16 (FIG. 1). Support 24 may prevent collapse of filter 18 while still substantially maximizing a free flow cross-sectional area through orifice 19 to reduce pressure drop across orifice 19 and inlet 14 with other shapes and/or coupling methods. The dimensions may be scaled to any size that allows apparatus 10 to function as described herein.

Figure 8:
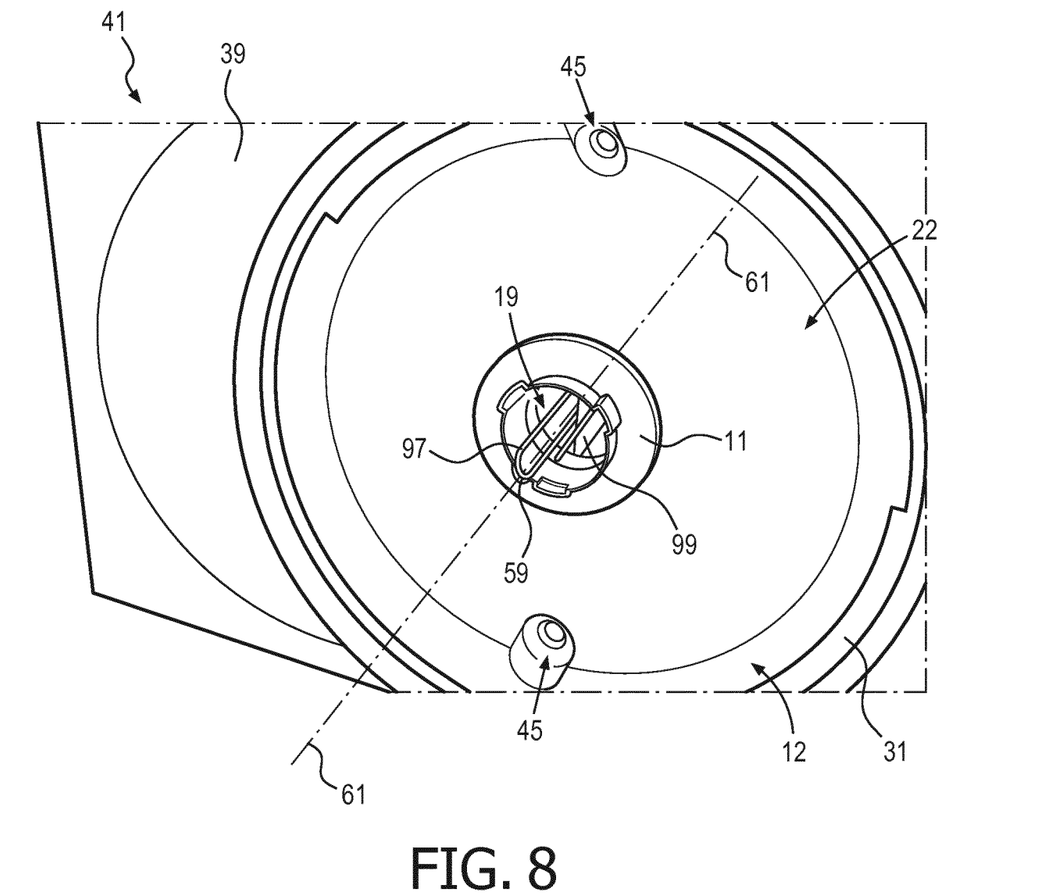
FIG. 8 illustrates another embodiment of the support.

For example, FIG. 8 illustrates another embodiment of support 24. In FIG. 8, support 24 is formed by a single arcuate component 97 clipped to a center portion 99 of orifice 19. In some embodiments, center portion 99 may be formed as part of body 12 and/or center portion 99 may be coupled to body 12 in and/or near orifice 19 so that it receives support 24 at orifice 19. In some embodiments, arcuate component 97 extends to the same protruding position 59 as the embodiment of support 24 shown in FIG. 7.

In some embodiments, arcuate component 97 may extend to a different positon depending on the properties (e.g., material, thickness, clipping mechanism, etc.) of arcuate component 97 and/or other factors, for example.

Figure 9:
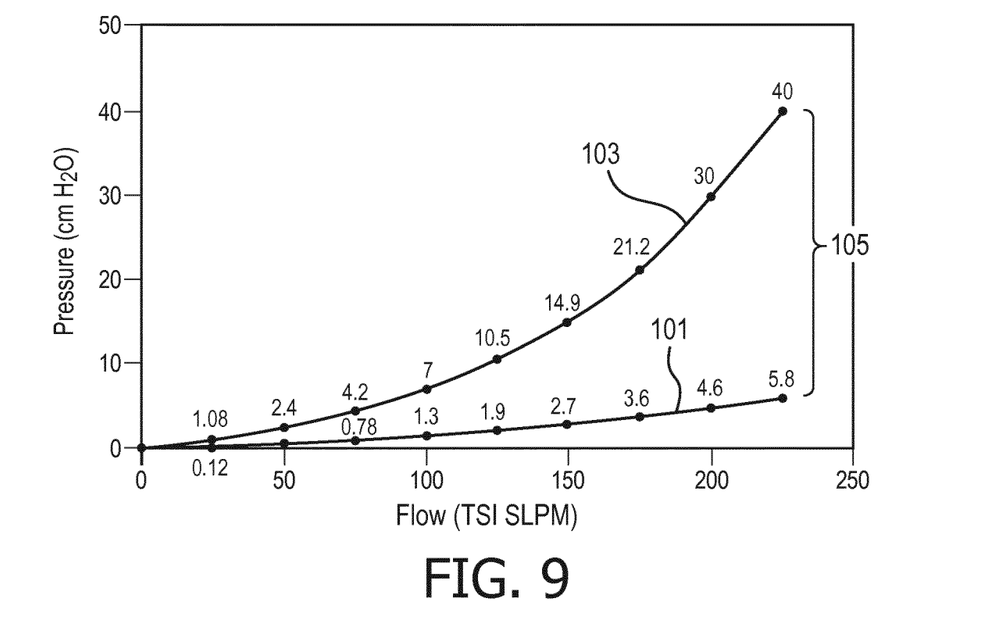
FIG. 9 illustrates a first pressure drop curve measured without the filter or the support installed in the muffler assembly, and a second pressure drop curve measured with the filter installed but not the support.
Figure 10:
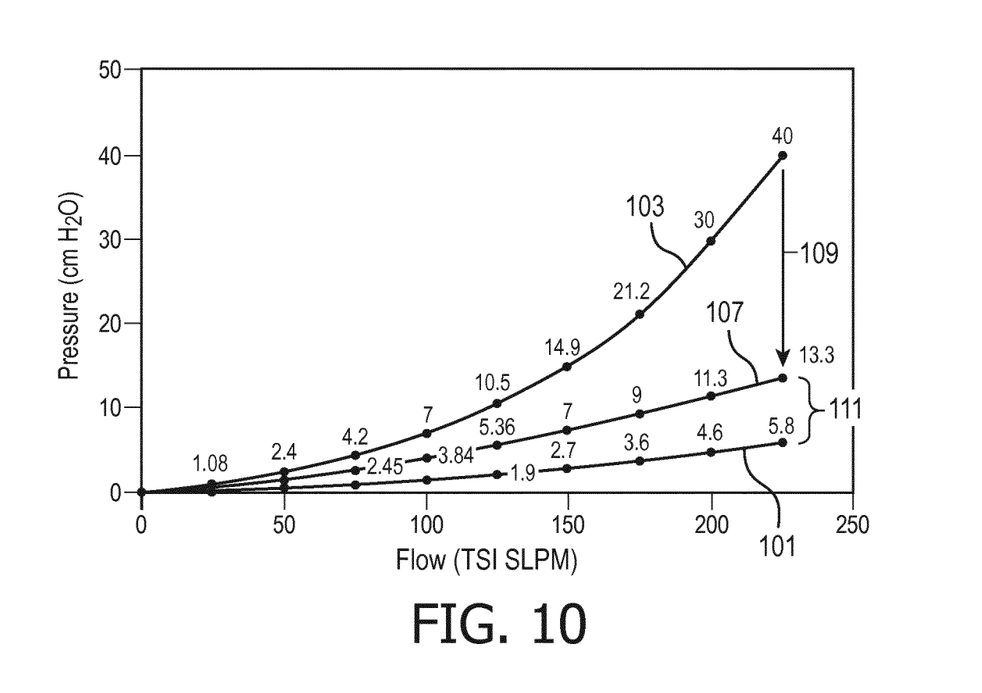
FIG. 10 illustrates the first and second pressure drop curves, and a third pressure drop curve measured with the filter and a first embodiment of the support installed.
Figure 11:
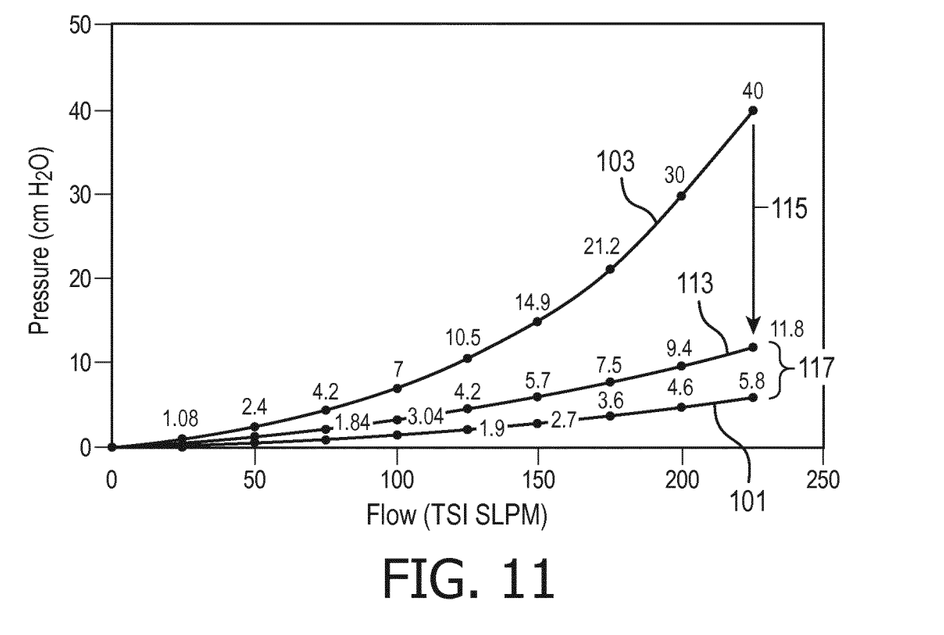
FIG. 11 illustrates the first and second pressure drop curves, and a fourth pressure drop curve measured with the filter and a second embodiment of the support installed.

FIG. 9-11 illustrate use of a pancake filter 18 (FIG. 2) in a muffler assembly 200 (FIG. 2) with and without support 24 (FIG. 2). FIG. 9-11 illustrate pressure drop at inlet 14 (FIG. 1) by way of pressure drop curves plotted on a pressure versus flow rate graph. FIG. 9 illustrates a first pressure drop curve 101 measured without pancake filter 18 or support 24 installed in muffler assembly 200 (e.g., for reference), and a second pressure drop curve 103 measured with pancake filter 18 installed but not support 24. There is a large (relative to FIGS. 10 and 11 described below) difference 105 between the two curves 101 and 103 because filter 18 likely collapsed into orifice 19 (FIG. 2) and/or inlet 14 during the measurements made for curve 103. FIG. 10 illustrates the first 101 and second pressure drop curves 103, and a third pressure drop curve 107 measured with filter 18 and a first embodiment (e.g., the embodiment illustrated in FIG. 2-7) of support 24 installed. FIG. 10 illustrates a pressure drop improvement 109 because filter 18 was supported by support 24. As shown in FIG. 10, with the installation of the first embodiment of support 24, the difference 111 between curves 101 and 107 is small compared to the difference 105 (FIG. 9) between curves 101 and 103. FIG. 11 illustrates the first 101 and second 103 pressure drop curves, and a fourth 113 pressure drop curve measured with filter 18 and a second embodiment (e.g., the embodiment illustrated in FIG. 8) of support 24 installed. Like FIG. 10, FIG. 11 illustrates a pressure drop improvement 115 because filter 18 was supported by support 24. As shown in FIG. 11, with the installation of the second embodiment of support 24, the difference 117 between curves 101 and 113 is small compared to the difference 105 (FIG. 9) between curves 101 and 103.

Returning to FIG. 1, pressure generator 16 is configured to generate a flow of gas for delivery to the airway of a subject 50. Pressure generator 16 may control one or more parameters of the flow of gas (e.g., flow rate, pressure, volume, temperature, gas composition, etc.) for therapeutic purposes, and/or for other purposes. By way of a non-limiting example, pressure generator 16 may be configured to control the flow rate and/or pressure of the flow of gas to provide pressure support to the airway of subject 12. Pressure generator 16 receives a flow of gas from a gas source, such as the ambient atmosphere through inlet 14, and/or other sources, and elevates the pressure of that gas for delivery to the airway of subject 50. Pressure generator 16 comprises one or more devices, such as, for example, a pump, blower, piston, bellows, and/or other devices that are capable of elevating the pressure of the received gas for delivery to subject 50. Pressure generator 50 may comprise one or more valves for controlling the pressure/flow of gas. The present disclosure also contemplates controlling the operating speed of a blower included in pressure generator 50, either alone or in combination with such valves, to control the pressure/flow of gas provided to the patient.

Gas delivery flow path 52 is configured to communicate the gas between pressure generator 16 and subject 50. As such, gas delivery flow path 52 comprises interface appliance 54, one or more conduits 56, and/or other components. One or more conduits 56 are configured to convey the pressurized flow of gas to interface appliance 54. One or more conduits 56 may comprise a flexible length of hose, and/or other conduits configured to communicate gas between pressure generator 16 and interface appliance 54.

Interface appliance 54 is configured to deliver the flow of gas to the airway of subject 50. In some embodiments, interface appliance 54 is configured to be non-invasively engaged by the mouth and/or nose of subject 50. Non-invasive engagement comprises removably engaging one or more external orifices of the airway of subject 50 (e.g., nostrils and/or mouth) to communicate gas between the airway of subject 50 and interface appliance 54. Some examples of non-invasive interface appliance 54 may comprise, for example, a nasal cannula, a nasal mask, a nasal/oral mask, a full face mask, a total face mask, and/or other interface appliances that communicate a flow of gas with an airway of a subject. In some embodiments, interface appliance 54 may include an invasive appliance, such as an endotracheal tube or other invasive appliances. The present disclosure is not limited to these examples, and contemplates delivery of the flow of gas to the subject using any interface appliance.

Although gas delivery flow path 52 is illustrated in FIG. 1 as a single-limbed interface for the delivery of the gas to the airway of subject 50, this is not intended to be limiting. The scope of this disclosure includes double-limbed circuits having a first limb configured to provide the flow of gas to the airway of the subject, and a second limb configured to selectively exhaust gas (e.g., to exhaust exhaled gases). Such a second limb may exhaust gas to the ambient atmosphere and/or may couple interface appliance 54 to inlet 14 of pressure generator 16, for example.

One or more system sensors 60 are configured to generate output signals conveying information related to one or more parameters of the gas within system 8 and/or other information. The one or more parameters of the gas within system 8 may comprise gas parameters related to the pressurized flow of breathable gas, breathing parameters related to respiration of subject 50, and/or other parameters. Sensors 60 may comprise one or more sensors that measure such parameters directly (e.g., through fluid communication with the flow of gas in interface appliance 54). Sensors 60 may comprise one or more sensors that generate surrogate output signals related to the one or more parameters indirectly. For example, sensors 60 may comprise one or more sensors configured to generate an output based on an operating parameter of pressure generator 16 (e.g., flow rate and/or pressure estimations from motor current, voltage, rotational velocity, and/or other operating parameters), and/or other sensors.

The one or more gas parameters of the pressurized flow of breathable gas may comprise, for example, one or more of a flow rate, a volume, a pressure, humidity, temperature, acceleration, velocity, one or more parameters related to a chemical composition of the gas, and/or other gas parameters. Breathing parameters related to the respiration of subject 50 may comprise a tidal volume, a timing (e.g., beginning and/or end of inhalation, beginning and/or end of exhalation, etc.), a respiration rate, a duration (e.g., of inhalation, of exhalation, of a single breathing cycle, etc.), respiration frequency, and/or other breathing parameters. Although sensor 60 is illustrated in FIG. 1 at only one location in system 8, this is not intended to be limiting. Sensors 60, for example, may comprise sensors disposed in a plurality of locations, such as at various locations within pressure generator 16, within (or in communication with) interface appliance 54, and/or other locations.

Controller 70 is configured to control pressure generator 16 to generate the flow of gas in accordance with a pressure support therapy regime and/or other therapy regimes. In some embodiments, the pressurized flow of gas generated by pressure generator 16 is controlled to replace and/or compliment a patient's regular breathing. Pressure support therapy may be used to maintain an open airway in a patient so that oxygen and carbon dioxide may be exchanged more easily, requiring little and/or no effort from the patient. By way of non-limiting example, controller 70 may control pressure generator 16 such that the pressure support provided to the subject via the flow of gas comprises continuous positive airway pressure support (CPAP), bi-level positive airway pressure support (BPAP), proportional positive airway pressure support (PPAP), forced oscillation technique, and/or other types of pressure support therapy.

CPAP supplies a fixed positive pressure to maintain a continuous level of positive airway pressure in a patient. BPAP provides a first inspiratory pressure (IPAP) and a second, typically lower, expiratory pressure (EPAP) for easier exhalation during ventilation. In some therapy modes (e.g., PPAP), controller 70 may control pressure generator 16 to apply variable pressure support in which the amount of pressure delivered to the patient during inhalation and/or during exhalation is determined and delivered on a breath by breath basis. In some embodiments, controller 70 may be configured to control pressure generator 16 to temporarily drop the supplied pressure during exhalation (C-Flex) to reduce exhalation effort required by the patent. In some embodiments, controller 70 is configured to control pressure generator 16 to deliver staged pressure support. In staged pressure support therapy, the pressure delivered by pressure generator 16 gradually increases over time. In some embodiments, controller 70 may control pressure generator 16 to switch therapy modes based on information related to the respiration of subject 50 and/or other information. For example, controller 70 may control pressure generator 16 to change from BPAP to CPAP after a certain number of breaths by subject 50. Controller 70 is configured to control pressure generator 16 based on information conveyed by the output signals from sensors 60, information entered by a user to user interface 90, information stored in electronic storage 80, and/or other information.

User interface 90 is configured to provide an interface between system 8 and subject 50 and/or other users through which subject 50 and/or other users may provide information to and receive information from system 8. Other users may comprise, for example, a caregiver, a doctor, and/or other users. This enables data, cues, results, and/or instructions and any other communicable items, collectively referred to as "information," to be communicated between a user (e.g., subject 50) and one or more of pressure generator 16, controller 70, and/or other components of system 8. For example, a user may specify one or more therapy regimes that are to be delivered to subject 50 using user interface 90. Controller 70 may then customize the therapy regime delivered to subject 50 based on the one or more inputs made by the user to the user interface. As another example, therapy pressures, the breath rate of subject 50, and/or other information may be displayed to a user (e.g., subject 50) via user interface 90.

Examples of interface devices suitable for inclusion in user interface 90 comprise a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 90 comprises a plurality of separate interfaces. In one embodiment, user interface 90 comprises at least one interface that is provided integrally with pressure generator 16 and/or controller 70.

It is to be understood that other communication techniques, either hard-wired or wireless, are also contemplated by the present disclosure as user interface 90. For example, the present disclosure contemplates that user interface 90 may be integrated with a removable storage interface provided by electronic storage 80. In this example, information may be loaded into system 8 from removable storage (e.g., a smart card, a flash drive, a removable disk, etc.) that enables the user(s) to customize the implementation of system 8. Other exemplary input devices and techniques adapted for use with system 8 as user interface 90 comprise, but are not limited to, an RS-232 port, RF link, an IR link, modem (telephone, cable or other). In short, any technique for communicating information with system 10 is contemplated by the present disclosure as user interface 90.

In some embodiments, electronic storage 80 comprises electronic storage media that electronically stores information. The electronic storage media of electronic storage 80 may comprise one or both of system storage that is provided integrally (i.e., substantially non-removable) with system 8 and/or removable storage that is removably connectable to system 8 via, for example, a port (e.g., a USB port, a firewire port, etc.) or a drive (e.g., a disk drive, etc.). Electronic storage 80 may comprise one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 80 may store software algorithms, information determined by controller 70, information received via user interface 90, and/or other information that enables system 8 to function properly. Electronic storage 80 may be (in whole or in part) a separate component within system 8, or electronic storage 80 may be provided (in whole or in part) integrally with one or more other components of system 8 (e.g., user interface 90, controller 70, pressure generator 16, etc.).

Information determined by controller 70 and/or stored by electronic storage 80 may comprise information related to respiration of subject 50, compliance, use frequency, and/or other information. The information stored by electronic storage 80 may be viewed via user interface 90, and/or other via other methods. The information stored by electronic storage 80 may be used, for example, to adjust settings, used by a doctor to make medical decisions, and/or for other uses. In some embodiments, system 8 may include a wireless transmitter (not shown) and the information determined by controller 70, the information stored by electronic storage 80, and/or other information may be communicated to a care giver, for example, over a wireless network.

Figure 12:
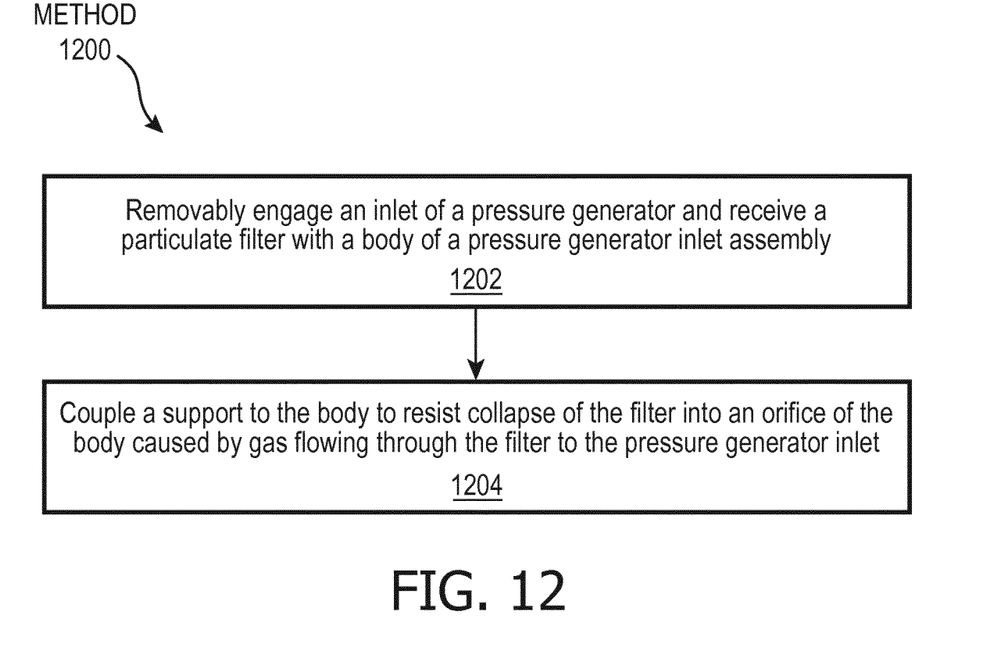
FIG. 12 illustrates a method for filtering gas drawn into a pressure generator with a pressure generator inlet apparatus.

FIG. 12 illustrates a method 1200 for filtering gas drawn into a pressure generator with a pressure generator inlet apparatus. The inlet apparatus comprises a body, a support, and/or other components. The operations of method 1200 presented below are intended to be illustrative. In some embodiments, method 1200 may be accomplished with one or more additional operations not described, and/or without one or more of the operations discussed. Additionally, the order in which the operations of method 1200 are illustrated in FIG. 12 and described below is not intended to be limiting.

At an operation 1202, an inlet of the pressure generator is removably engaged with the body of the pressure generator inlet apparatus. At operation 1202, the body receives a particulate filter. The body forms an orifice configured to conduct gas that has passed through the filter to the pressure generator inlet. In some embodiments, the filter is a two-sided disc filter. In some embodiments, the two-sided disc filter is a pancake filter. In some embodiments, the body couples with the inlet on a first side of the body and receives the filter on a second side of the body opposite the first side. In some embodiments, operation 1202 is performed by a body the same as or similar to body 12 (shown in FIG. 2 and described herein).

At an operation 1204, the support is coupled to the body. The support is coupled to the body at or near the orifice. The support is configured to extend from the body toward the filter and support the filter. The support resists collapse of the filter into the orifice of the body caused by gas flowing through the filter to the pressure generator inlet. In some embodiments, the support is a protrusion, and the protrusion extends from the second side of the body toward the filter and supports the filter. In some embodiments, responsive to being received by the body, a first side of the pancake filter engages the second side of the body, and the protrusion extends past the first side of the pancake filter into an inside of the pancake filter to support a second, opposite, side of the pancake filter from the inside.

In some embodiments, the protrusion comprises three arcuate members and/or other components. An individual arcuate member has one end coupled to an edge of the inlet orifice at or near the second side of the body and an opposite end coupled to the other arcuate members in a protruding position relative to the second side of the body. In some embodiments, the inlet orifice has a circular cross-section with a central axis, and the opposite ends of the arcuate members are coupled in the protruding position at a location that corresponds to the central axis of the circular inlet orifice. In some embodiments, operation 1204 is performed by a support the same as or similar to support 24 (shown in FIG. 2 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. An apparatus, comprising:
 a medical ventilator comprising a pressure generator configured to provide a pressurized flow of breathable gas to a patient to replace or complement breathing of the patient;
 a body configured to receive a two-sided disc particulate filter and to removably engage an inlet of the pressure generator, the body forming an orifice configured to conduct the pressurized flow of breathable gas drawn by the pressure generator through the filter to the inlet; and
 a support extending from the body at or near a periphery of the orifice toward a central axis of the orifice, over at least a portion of the orifice, and between at least a portion of the filter and the orifice to support the filter, the support configured to resist collapse of the filter into the orifice caused by the pressurized flow of breathable gas flowing through the filter to the pressure generator inlet;
 wherein the body is configured to couple with the inlet on a first side of the body and receive a first side of the filter on a second side of the body opposite the first side of the body, and
 wherein the support is a protrusion configured to extend from the second side of the body and resist collapse of the filter.

2. The apparatus of claim 1, wherein the two-sided disc particulate filter is a pancake filter.

3. The apparatus of claim 2, wherein, responsive to being received by the body, the first side of the pancake filter engages the second side of the body, and the protrusion extends past the first side of the pancake filter into an inside of the pancake filter to support the second, opposite, side of the pancake filter from the inside.

4. The apparatus of claim 2, wherein the pancake filter is a continuous disc shape.

5. The apparatus of claim 4, wherein the pancake filter covers the orifice and the body directs substantially all of the pressurized flow of the breathable gas through the pancake filter;
 the pressure generator configured to provide the pressurized flow of breathable gas up to about 40 cmH$_2$O at up to about 225 lpm.

6. The apparatus of claim 1, wherein the protrusion comprises three arcuate members, an individual arcuate member having one end coupled to an edge of the orifice at or near the second side of the body and an opposite end coupled to the other arcuate members in a protruding position relative to the second side of the body.

7. The apparatus of claim 6, wherein the orifice has a circular cross-section with a central axis, and wherein the opposite ends of the arcuate members are coupled in the protruding position at a location that corresponds to the central axis of the circular orifice.

8. A method for filtering gas drawn into a medical ventilator comprising a pressure generator configured to provide a pressurized flow of breathable gas to a patient to replace or complement breathing of the patient via a pressure generator inlet apparatus, the apparatus comprising a body and a support, the method comprising:
 removably engaging, with the body, an inlet of the pressure generator and receiving, with the body, a two-sided disc particulate filter, the body forming an orifice configured to conduct the pressurized flow of breathable gas drawn by the pressure generator through the filter to the pressure generator inlet;
 the support extending from the body at or near a periphery of the orifice toward a central axis of the orifice, over at least a portion of the orifice, and between at least a portion of the filter and the orifice to support the filter, the support configured to resist collapse of the filter into the orifice caused by the pressurized flow of breathable gas flowing through the filter to the inlet;

wherein the body couples with the inlet on a first side of the body and receives a first side of the filter on a second side of the body opposite the first side of the body, and wherein the support is a protrusion that extends from the second side of the body towards the filter.

9. The method of claim 8, wherein the two-sided disc particulate filter is a pancake filter.

10. The method of claim 9, wherein, responsive to being received by the body, the first side of the pancake filter engages the second side of the body, and the protrusion extends past the first side of the pancake filter into an inside of the pancake filter to support the second, opposite, side of the pancake filter from the inside.

11. The method of claim 9, wherein the pancake filter is a continuous disc shape.

12. The method of claim 11, wherein the pancake filter covers the orifice and the body directs substantially all of the pressurized flow of the breathable gas through the pancake filter;

the pressure generator configured to provide the pressurized flow of breathable gas up to about 40 cmH$_2$O at up to about 225 lpm.

13. The method of claim 8, wherein the protrusion comprises three arcuate members, an individual arcuate member having one end coupled to an edge of the orifice at or near the second side of the body and an opposite end coupled to the other arcuate members in a protruding position relative to the second side of the body.

14. The method of claim 8, wherein the protrusion comprises one or more protrusions that extend from the second side of the body over at least the portion of the orifice and towards a central axis of the orifice.

15. An apparatus comprising:

a medical ventilator comprising a pressure generator means for providing a pressurized flow of breathable gas to a patient to replace or complement breathing of the patient;

means for removably engaging an inlet of the pressure generator means and receiving a two-sided disc particulate filter, the means for engaging and receiving forming an orifice configured to conduct gas drawn by the pressure generator means through the filter to the inlet; and means for supporting the filter, the means for supporting extending from the means for removably engaging at or near a periphery of the orifice, toward a central axis of the orifice, over at least a portion of the orifice, and between at least a portion of the filter and the orifice to support the filter, the means for supporting configured to resist collapse of the filter into the orifice caused by the pressurized flow of breathable gas flowing through the filter to the inlet;

wherein the means for engaging and receiving couples with the inlet on a first side of the means for engaging and receiving, and receives a first side of the filter on a second side of the means for engaging and receiving, opposite the first side of the means for engaging and receiving, and wherein the means for supporting includes a protrusion that extends from the second side of the means for engaging and receiving towards the first side of the filter.

16. The apparatus of claim 15, wherein the two-sided disc particulate filter is a pancake filter.

17. The apparatus of claim 16, wherein the pancake filter is a continuous disc shape.

18. The apparatus of claim 17, wherein the pancake filter covers the orifice and the means for engaging and receiving directs substantially all of the pressurized flow of the breathable gas through the pancake filter;

the pressure generator means configured to provide the pressurized flow of breathable gas up to about 40 cmH$_2$O at up to about 225 lpm.

19. The apparatus of claim 15, wherein the protrusion comprises three arcuate members, an individual arcuate member having one end coupled to an edge of the orifice at or near the second side of the means for engaging and receiving, and an opposite end coupled to the other arcuate members in a protruding position relative to the second side of the means for engaging and receiving.

20. The apparatus of claim 15, wherein the protrusion comprises one or more protrusions that extend from the means for removably engaging and over at least the portion of the orifice and towards a central axis of the orifice.

* * * * *